US00PP16253P3

(12) United States Plant Patent
Evers

(10) Patent No.: US PP16,253 P3
(45) Date of Patent: Feb. 14, 2006

(54) HYBRID TEA ROSE PLANT NAMED 'TAN01549'

(50) Latin Name: *Rosa hybrida*
Varietal Denomination: TAN01549

(75) Inventor: Christian Evers, Uetersen (DE)

(73) Assignee: Rosen Tantau Mahias Tantau Nachfolger, Uetersen (DE)

( * ) Notice: Subject to any disclaimer, the term of this patent is extended or adjusted under 35 U.S.C. 154(b) by 75 days.

(21) Appl. No.: 10/899,799

(22) Filed: Jul. 26, 2004

(65) Prior Publication Data

US 2005/0204439 P1 Sep. 15, 2005

(51) Int. Cl.
*A01H 5/00* (2006.01)

(52) U.S. Cl. ..... Plt./140

(58) Field of Classification Search ..... Plt./140
See application file for complete search history.

*Primary Examiner*—Anne Marie Grunberg
*Assistant Examiner*—Annette H Para
(74) *Attorney, Agent, or Firm*—Klarquist Sparkman LLP

(57) ABSTRACT

Hybrid tea rose plant for cut flower production having high production of flowers—(240–260 flowers per m2/year) of long lasting flowers (15–18 days).

1 Drawing Sheet

Figure 1:
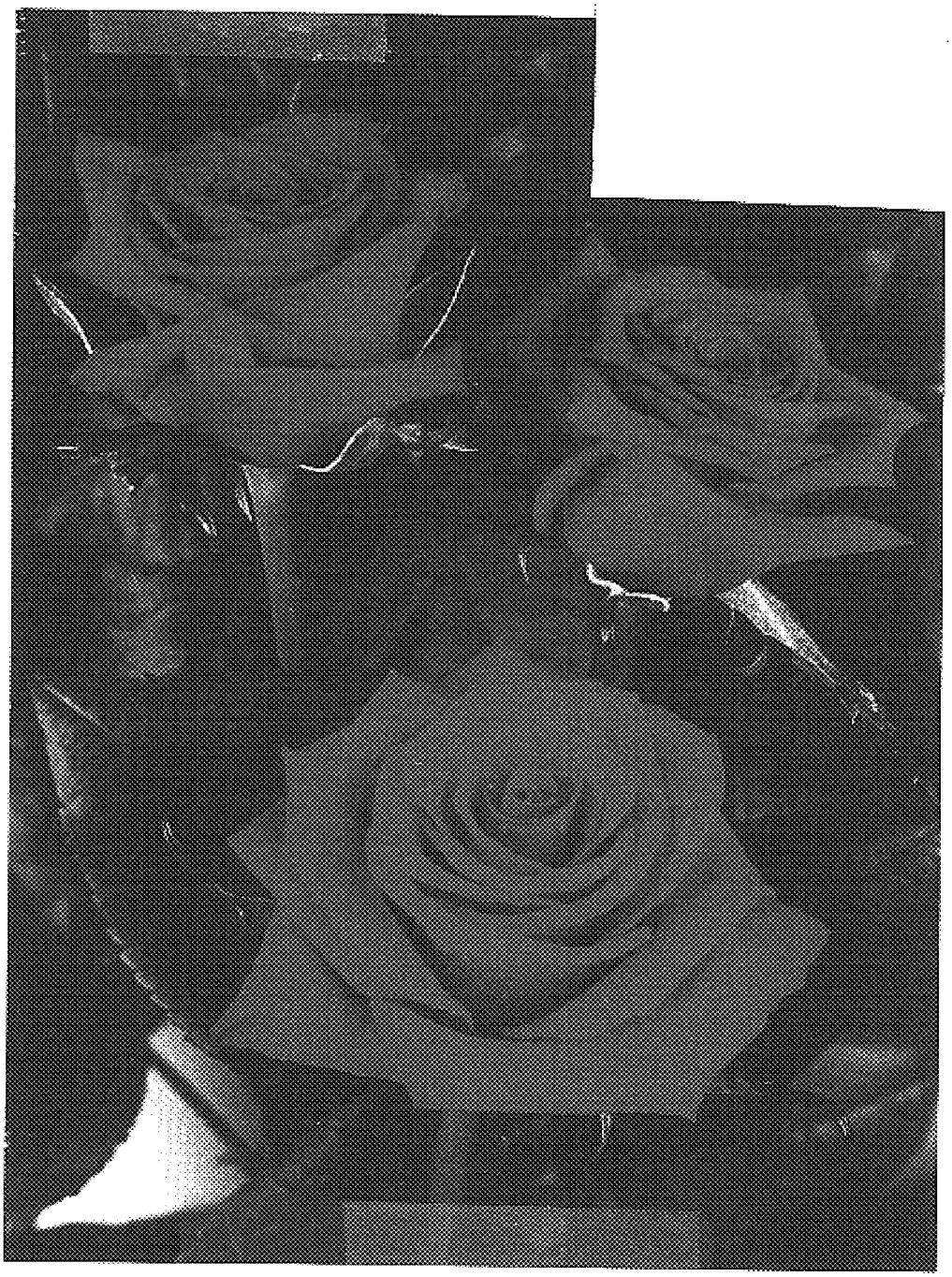

Genus and species: *Rosa hybrida*.
Varietal denomination: 'TAN01549'.

SUMMARY OF THE INVENTION

The present invention relates to a new and distinct variety of hybrid tea rose plant for cut flower production, which was originated by me by cross-breeding two unnamed red hybrid tea rose plants.

BACKGROUND OF THE INVENTION

The primary objective of this breeding was to produce a new rose variety for cut rose production of flowers having a high vase life with good production of flowers per plant.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Long lastingness of cut flowers (up to 18 days).
2. High production of flowers: (240–260 flowers per m2/year).

Asexual reproduction of this new variety by cuttings, as performed at Uetersen, Germany, shows that the foregoing and all other characteristics and distinctions come true to form and are established and transmitted through succeeding propagations.

Comparison with Parents

'TAN01549' has a longer stem than the mother variety and a darker color of flower than the father variety.

Comparison with Similar Variety

The color of the flowers of 'TANolorak' are much darker than those of 'TAN01549' and 'TANolorak' is perfumed whereas 'TAN01549' is not.

BRIEF DESCRIPTION OF THE ILLUSTRATION

The accompanying illustration shows typical specimens of flowers of this new variety depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—Unnamed seedling (unpatented).
*Pollen parent.*—Unnamed seedling (unpatented).

FLOWER

Observations made from plants of one year of age grown in a greenhouse environment at Uetersen, Germany.

Blooming habit: Continuous.
Bud:
*Size.*—About 4 cm long and 5.5 cm in diameter long when the petals start to unfurl.
*Form.*—The bud form is long.
*Color.*—When sepals first divide, bud color is Red Group 46A. When half blown, the upper sides of the petals are Red Group 46B; and the lower sides of the petals are Red Group 46B.
*Sepals.*—Color: Upper surface: Green Group 132A. Lower surface: Green Group 132D. Length: 6.5 cm.

Width: 3.6 cm. Shape: Elongate, pointed. Surface texture: Smooth. There are three heavily appendaged sepals. There are four unappendaged sepals with glandular edges.

*Receptacle*.—Color: Green Group 143C. Shape: Funnel. Size: Medium, 0.8 cm by 1.3 cm. Surface: Smooth.

*Peduncle*.—Length: Medium, averaging about 8 cm. Surface: Smooth. Color: Green Group 143C. Strength: Erect.

Bloom:

*Size*.—Large. Average open diameter is about 8.7 cm.

*Borne*.—Singly.

*Stems*.—Strength: Strong. Average length is about 50 cm–70 cm and 0.6 cm in diameter.

*Form*.—When first open: Cupped. Permanence: Retains its form to the end.

*Petalage*.—Number of petals under normal conditions: 27.

*Color*.—The upper sides of the petals are Red Group 46B. The reverse sides of the petals are Red Group 46B. The base of each petal has a small bright yellow spot, Yellow Group 21A. The major color on the upper side is Red Group 46B.

*Variations*.—None.

*Discoloration*.—The general tonality at the end of the first day: Red Group 46B and at the end of the third day is Red Group 46B.

*Fragrance*.—None.

Petals:

*Texture*.—Leathery, thin.

*Surface*.—Smooth.

*Shape*.—Heart-shaped.

*Size*.—Width: 6.6 cm. Length: 5 cm.

*Margin*.—Smooth. Apex Shape: Blunt. Base Shape: Blunt.

*Form*.—Edges slightly quilled.

*Arrangement*.—Irregular.

*Petaloids*.—Number: 3. Color: Red Group 46B.

*Persistence*.—Petals hang on and dry.

*Lastingness*.—On the plant: Long, about 15–18 days. As a cut flower: Long, about 15–18 days.

Reproductive parts:

*Stamens*.—Number: 96. Length: 0.3 cm. Anthers: Length: 0.2 cm. Color: Yellow-Orange Group 23A. Arrangement: Filaments: Color: Red-Orange Group 33A. Length: 0.6 cm. Pollen: Color: Yellow-Orange Group 23A.

*Pistils*.—Number: 84. Length: 0.7 cm. Styles: Color: Yellow-Orange Group 23C. Length: 0.6 cm. Stigmas: Color: Orange-Yellow Group 24D. Length: 0.1 cm.

*Hips*.—None produced.

PLANT

*Form*.—Shrub like Tea Rose.

*Growth*.—Vigorous.

*Mature plant*.—Height: 120 cm. at 1 year. Width: 50 cm.

Foliage: Number of leaflets on normal mid-stem leaves: 5.

*Size*.—Large (16 cm long×13 cm wide).

*Quantity*.—Normal.

*Color*.—New foliage: Upper side: Green Group 147A. Lower side: Green Group 147B. Old foliage: Upper side: Green Group 147A. Lower side: Green Group 147B.

Leaflets:

*Size*.—About 8 cm long×6 cm wide.

*Shape*.—Pointed oval.

*Base shape*.—Blunt.

*Apex shape*.—Pointed.

*Texture*.—Upper side: Leathery.

*Edge*.—Serrated.

*Serrations*.—Single.

*Petiole*.—Color: Green Group 147D.

*Petiole rachis*.—Color: Green Group 147D. Underside: Smooth.

*Stipules*.—Length: 1.2 cm.

*Disease resistance*.—Not tested.

*Pest resistance*.—Not tested.

*Vein color*.—Green Group 147C.

*Venation pattern*.—Pyramidal.

Wood:

*New wood*.—Color: Green Group 144B. Bark: Smooth.

*Old wood*.—Color: Brown-Orange Group 175B. Bark: Rough.

Prickles:

*Quantity*.—On main canes from base: 12 per 63 cm length of stem.

*Form*.—Hooked downward.

*Length*.—0.8 cm.

*Color when young*.—Yellow-Green Group 144A.

*Color when mature*.—Greyed-Green Group 189A.

Small prickles:

*Quantity*.—On main stalks: Few. On laterals: Few. Color: When young: Yellow-Green Group 149A. When mature: Yellow-Green Group 144A.

Winter hardiness: Not tested.

I claim:

1. A new and distinct variety of rose plant of the hybrid tea class, substantially as herein shown and described, characterized particularly by its high production of flowers and the long lastingness of cut flowers.

* * * * *